United States Patent

Cohen et al.

[11] Patent Number: 6,068,652
[45] Date of Patent: May 30, 2000

[54] METHOD AND MEANS FOR CALCULATING ELECTRODE FREQUENCY ALLOCATION

[76] Inventors: Lawrence T. Cohen, 116 Katrina Street, Blackburn North. Victoria 3130, Australia; Jin Xu; Shiang Xu, both of 11 Clay Drive, Doncaster, Victoria 3108, Australia; Colette McKay, 23 Crisp Street, Essendon. Victoria 3040., Australia; Michael Marsh, 10716 St. Michael Ct., Fort Smith. Arkansas, Ark. 72908; Andrew T. Mortlock, 6/8-10 Helen Street, Lane Cove. N.S.W. 2066, Australia; Peter J. Blamey, 36 Oakhill Road, Mount Waverley. Victoria 3149, Australia; Lesley A. Whitford, 11 Stuart Street, Armadale. Victoria 3143, Australia

[21] Appl. No.: 09/040,355

[22] Filed: Mar. 10, 1998

[51] Int. Cl.$^7$ .............................. A61N 1/08; H04R 25/00
[52] U.S. Cl. ................................ 607/57; 600/25; 600/559
[58] Field of Search ..................................... 607/2, 55–57, 607/59, 137, 136; 623/10; 600/559, 379, 554, 25

[56] References Cited

PUBLICATIONS

"A cochlear frequency–position function for several species–29 years later" J. Acoust. Soc. Am. 87, 2592–2605, by Greenwood, D.D. (1990).

"Cellular pattern and nerve supply of the human organ of Corti" Bredberg, G. (1968). Acta Otolaryngol. (Stockh.) Suppl. 236, 1–138.

"Radiology evaluation of multiple—channel intracochlear implant insertion depth" Am. J. Otol. 14, 386–391 by Marsh, M.A., Xu, J., Blamey, P.J., Whitford, L.A., Xu, S.A., Silverman, J.M, and Clark, G.M. (1993).

"Cochlear View' and its application in cochlear implant patients" Marsh et al. (1993) and Xu, J., Xu, S.A., Clark, G.M., and Marsh, M.A. (1994).

"Computer–aided three–dimensional reconstruction in human cochlear maps: measurement of the lengths of organ of Corti, outer wall, inner wall, and Rosenthal's canal," Ann. Otol. Rhinol. Laryngol. (In press) Kawano. A.. Seldon H.L.. and Clark, G.M.

*Primary Examiner*—Kennedy J. Schaetzle

[57] ABSTRACT

There is provided a system for predicting the characteristic frequency of each electrode of an implanted cochlear electrode array from electrode position data contained in an image of the implanted cochlea. There is also provided a system for setting the frequency range to electrode map of a cochlear prosthesis.

18 Claims, 9 Drawing Sheets

METHOD AND MEANS FOR CALCULATING ELECTRODE FREQUENCY ALLOCATION

TECHNICAL FIELD

This invention relates to cochlear implants, and in particular to frequency allocation for particular electrodes in a multichannel cochlear implant.

BACKGROUND ART

Cochlear implants are used to provide a sensation of hearing to hearing impaired persons. Typically, the implant provides stimuli via a set of electrodes formed into an array which is inserted into the scala tympani of the patient. The cochlear implant system presents electrical stimulation directly to the auditory nerve fibres of the basilar membrane. The electrodes are driven via an implanted receiver stimulator unit. The implanted receiver stimulator unit produces stimulations in accordance with commands originating from an external speech processor. A preferably transcutaneous link transfers power and commands from the speech processor unit to the receiver stimulator.

The inner ear of a normally hearing person includes hair cells which convert the displacement of the basilar membrane in response to sound into nervous impulses. Different parts of the basilar membrane of the normal cochlea are displaced maximally by different frequencies of sound so that low frequency sounds maximally displace apical portions whereas higher frequency sounds cause displacement of more basal portions of the membrane. The nervous system is arranged so that a nervous impulse originating from a hair cell located adjacent an apical area of the membrane is perceived as a low frequency sound whereas a nervous impulse originating from a hair cell located adjacent a more basal position of the membrane is perceived as a higher frequency sound. The frequency which causes maximal displacement of the basilar membrane at a given position will hereinafter be referred to as the "characteristic frequency" at that position.

In a dysfunctional ear the hair cells may be damaged or absent so that no nervous impulses are generated. In such a case electrical stimulation impulses must be provided artificially to simulate the nervous activity of the hair cells in order to create a perception of sound. Such stimulation impulses are provided via the electrodes of a multi-channel cochlear electrode array. The array is arranged to follow at least part of the length of the basilar membrane and its electrodes are selectively driven to deliver electrical stimulations. In order to simulate a given sound it is necessary to firstly analyse that sound and break it down into essential features. This analysis can be in accordance with many different schemes and is performed by the speech processor. The speech processor then determines which electrodes of the array should be stimulated in order to best simulate the sound. For example, if the sound contains mainly high frequency components then it is best simulated by stimulation via basally located electrodes.

In order to determine the electrode to be stimulated for a given sound the speech processor makes use of a frequency range to electrode map, usually stored in an EPROM, which matches bands of sound frequencies to one or more electrodes of the electrode array. The frequency range mapped to each electrode is adjustable by the speech processor so that a characteristic frequency is allocated for each stimulating electrode. Existing methods for allocating frequency ranges to the electrodes are to use an educated guess or a longhand calculation to determine the characteristic frequency for each electrode and to choose frequency ranges consistent with the characteristic frequencies calculated for the electrodes.

It is accordingly desirable to be able to predict with some accuracy the characteristic frequency for each electrode of an implanted electrode array, so as to provide a reliable basis on which the allocation of frequency range to electrode mapping is made.

An article entitled "A cochlear frequency-position function for several species-29 years later" J. Acoust. Soc. Am. 87, 2592–2605, by Greenwood, D. D. (1990) describes the relationship between frequency and the site of maximal displacement of the basilar membrane expressed as a percentage of the total length of the organ of Corti, measured from the apex. The technique in this paper is not applicable to cochlear implants.

An article "Cellular pattern and nerve supply of the human organ of Corti" Bredberg, G. (1968).Acta Otolaryngol. (Stockh.) Suppl. 236, 1–138 describes temporal bone studies that establish a relationship between the percentage length along the organ of Corti and the angle in degrees about the modiolus relative to the basal end of the organ of Corti. This paper is not applicable to cochlear implants.

An article by Marsh, M. A., Xu, J., Blamey, P. J., Whitford, L. A., Xu, S. A., Silverman, J. M, and Clark, G. M. (1993). "Radiological evaluation of multiple-channel intracochlear implant insertion depth" Am. J. Otol. 14, 386–391 describes a method to document insertion depths of the electrode array from an X-ray. The paper identifies a difficulty in relating the angles that might be derived from the authors' method to the angles measured by Bredberg.

The above papers do not provide a clinically applicable method of accurately deriving the appropriate frequency ranges to be allocated to the electrode bands of a cochlear implant. Prior methods were based on the surgeon's reports, which the Marsh et al. paper states are inaccurate. Inaccurate prediction of the electrode/frequency correspondence leads to input frequencies mapped to the wrong sites in the cochlea. Such mis-mapping of electrodes may well result in a reduction in the comprehensibility and naturalness of sounds perceived by the implanted subject relative to that which would otherwise have been possible.

SUMMARY OF INVENTION

According to a first aspect of the present invention there is provided an apparatus for configuring the frequency range to electrode map of a cochlear implant prosthesis, the frequency range to electrode map containing frequency range to electrode mapping data, comprising:

a) processing means for processing electrode location data, the electrode location data describing the location of at least two electrodes relative to a cochlea, the electrodes being components of an electrode array, the processing means generating characteristic frequency data for use in determining a frequency range to electrode mapping;

b) input means for conveying the electrode location data to the processing means;

c) interface means for transferring the frequency range to electrode mapping to the frequency range to electrode map; characterised in that, the processing means generates the characteristic frequency data according to a characteristic frequency model, wherein the characteristic frequency data includes characteristic frequencies of electrodes of the electrode array, the characteristic frequency of an electrode corresponding to the estimated frequency of maximal displacement of the basilar membrane of the cochlea, according to the characteristic frequency model, at the location of said electrode of the electrode array.

According to a further aspect of the present invention there is provided a method for setting the frequency range to electrode map of a cochlear implant prosthesis including the steps of:

a) determining two fitting values by reference to an implanted electrode array the electrode array being implanted within a cochlea;

b) matching a template cochlear spiral to said electrode array according to the fitting values;

c) determining the position of each electrode of said electrode array spiral relative to the cochlea from the template cochlear spiral and known dimensions of the type of implanted array;

d) calculating a characteristic frequency for each electrode from the position of each electrode relative to the cochlea according to a mathematical model of the characteristic frequency characteristics of a cochlea for each of the electrodes;

e) setting the frequency range to electrode map of the cochlear implant prosthesis on the basis of the characteristic frequencies calculated in the previous step.

According to a final aspect of the present invention there is provided a software product for determining characteristic frequencies for electrodes in an implanted intracochlear electrode array based on an diagnostic medical image, said product being provided with inputs including for a given implanted array a first value being the number of electrodes extending outside the round window, and a second value being the number of electrodes extending from the round window to the most apical of a set of geometrically defined points on the diagnostic medical image to which the image of the array extends and identifying the most apical of said points, said product including means for determining the position of the implanted electrodes by reference to a predefined reference shape and predefined dimensions of the electrode array, means for mapping said electrode positions to corresponding characteristic frequencies, and means for outputting a set comprising characteristic frequencies for each electrode.

The present invention allows for an automated mapping calculation which requires only the counting of numbers of electrodes between certain clearly visualisable points on a diagnostic medical image of a cochlear. From this electrode count the characteristic frequencies for all electrodes are computed automatically. The output of this calculation can be used by the speech processor with or without a clinician's intervention to allocate a frequency range to each electrode.

According to one embodiment the present invention facilitates a clinician's obtaining of the electrode characteristic frequency information for a given patient by entering data readily derived from a diagnostic image, such as an X-ray, of the implanted cochlea. The present invention permits the position of each electrode of the cochlear electrode array to be determined automatically, with greater accuracy than is possible with prior art techniques.

According to a further embodiment of the present invention it is envisaged that the data contained in the diagnostic medical image would be extracted by means of an optical scanner and appropriate image signal processing.

Finally, it is also envisaged that the data output of the medical diagnostic image forming device be analysed by a computer running image signal processing software to extract the required electrode location data and that the electrode location data be interfaced directly to the apparatus of the invention automatically and without manual intervention.

BRIEF DESCRIPTION OF THE DRAWINGS

A preferred implementation of the present invention will now be described with reference to the accompanying drawings, in which.

DESCRIPTION

The present invention is described in the context of the cochlear implant devices available commercially from Cochlear Limited of 14 Mars Road, Lane Cove 2066 Australia. However, it will be appreciated that the present invention may equally be implemented with alternative electrode arrays. The apparatus, method, and software product herein described may be readily implemented in a variety of ways. Alternative calculation techniques may be used to those illustrated, particularly based upon the general principle that the location of the electrodes and hence the characteristic frequency may be determined from the geometry of the cochlea and the dimensions of the electrode array, once some characteristics of the extent of insertion are known.

Figure 1:
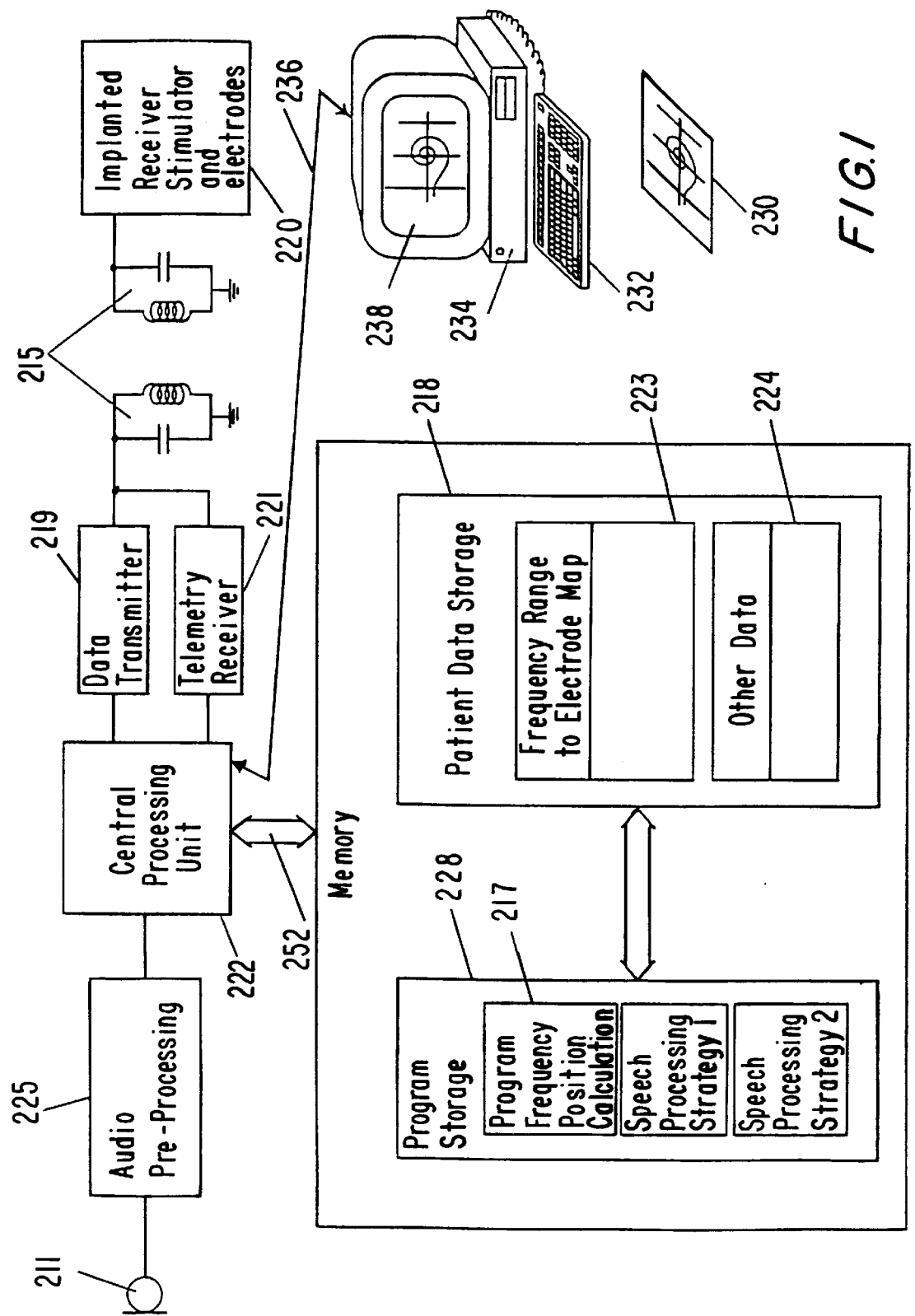
FIG. 1 is a schematic diagram of a cochlear implant prosthesis interfaced with a microprocessor for configuring the frequency band to electrode map of the cochlear prosthesis according to the present invention.

Referring to FIG. 1 there is depicted a schematic diagram of a cochlear implant prosthesis interfaced to a processing means in the form of microcomputer 250.

During standard operation the cochlear implant prosthesis functions as follows. A microphone 211 monitors ambient sounds, for example speech, and converts those sounds to electrical impulses. The audio pre-processing module 225 then performs various operations such as bandpass filtering, application of AGC and analogue to digital conversion. The digital signal is then analysed by the central processing unit 222 according to a speech processing strategy stored in program storage memory 228. The speech processing strategy determines by which electrodes the stimulations are to be delivered in order to best simulate the ambient sound by interrogating the frequency range to electrode allocation map 223 by means of bidirectional bus 252. The central processing unit 222 generates commands for the receiver stimulator 220 specifying the electrodes by which the stimulation is to be delivered and the amplitude and duration of the stimulation. The commands are encoded by the data transmitter 219 and sent via transcutaneous link 215 to the implanted receiver stimulator. The receiver stimulator decodes the commands and the applies stimulation via the specified electrodes thereby eliciting sound perceptions in the implanted subject.

By one embodiment of the invention an X-ray 230 of the cochlea with implanted electrode array is produced and referred to by an operator (not shown). Although an X-ray is used in the presently described embodiment other suitable medical imaging techniques could also be used to produce the necessary images. The operator visualises reference lines on the X-ray relative to certain anatomical landmarks therein depicted. Data concerning the position of the electrode array relative to the basilar membrane is then entered into a processing means 234. The microcomputer runs a program which contains a model of the cochlea suitable for generating the characteristic frequency of each electrode. On the basis of the calculated characteristic frequencies a frequency range to electrode map is generated either automatically according to preset instructions or with additional input from a clinician. The frequency range to electrode map is then downloaded from the microcomputer 250 to the speech processor by an interface means 236. This means could be a serial data connection, for example an RS232 or IIC interface as is well known in the art. The data is then transferred to patient data storage 218 where it becomes the frequency range to electrode allocation map of the speech processor.

In FIG. 1 the processing means which calculates the characteristic frequencies is a microcomputer and is distinct from the central processing unit 222 of the cochlear implant prosthesis. By a further embodiment however the calculations performed by microcomputer 250 are undertaken by the processing means of the cochlear implant speech processor 222 and the software required to calculate the characteristic frequencies stored within the cochlear implant prosthesis program storage memory 228 as characteristic frequency calculation program 217. According to this further embodiment of the invention it is simply necessary to transmit positional data concerning the location of the electrode array to the central processing unit 222 where the characteristic frequencies are calculated and the frequency range to electrode map updated.

Whilst the embodiment depicted in FIG. 1 relies on a human operator to visually locate various landmarks on the X-ray, or other diagnostic image, and enter them into the processing means by some means such as the keyboard 232 it would also be possible to use more highly automated methods. For example the X-ray could be inserted into a scanner and pattern recognition methods used to locate the landmarks whose position would then be transferred to the processing means. Alternatively an X-ray machine or other medical imaging equipment could be either directly, or via electronic data storage means, coupled to an image processing means interfaced to processor 234 so that no hardcopy of the X-ray or manual data entry would be required.

The method by which the data necessary to calculate the characteristic frequencies of the electrodes is extracted from the X-ray will now be explained.

The present invention is designed to be implemented after surgical implantation has been performed. It will be appreciated that variations in anatomy and in the extent of insertion of the array mean that the positioning of the electrode array will differ for each patient, and the present invention is intended to provide an accurate method of determining characteristic frequency for each implanted array.

After the electrode array is implanted, an X-ray (or other suitable medical image) of the cochlea is produced, preferably using the "Cochlear View" orientation of the patient's head as described by Marsh et al. (1993) and Xu, J., Xu, S. A., Clark, G. M., and Marsh, M. A. (1994), "'Cochlear View' and its application in cochlear implant patients," International Cochlear Implant, Speech and Hearing Symposium 1994, Melbourne Australia.

Figure 2:
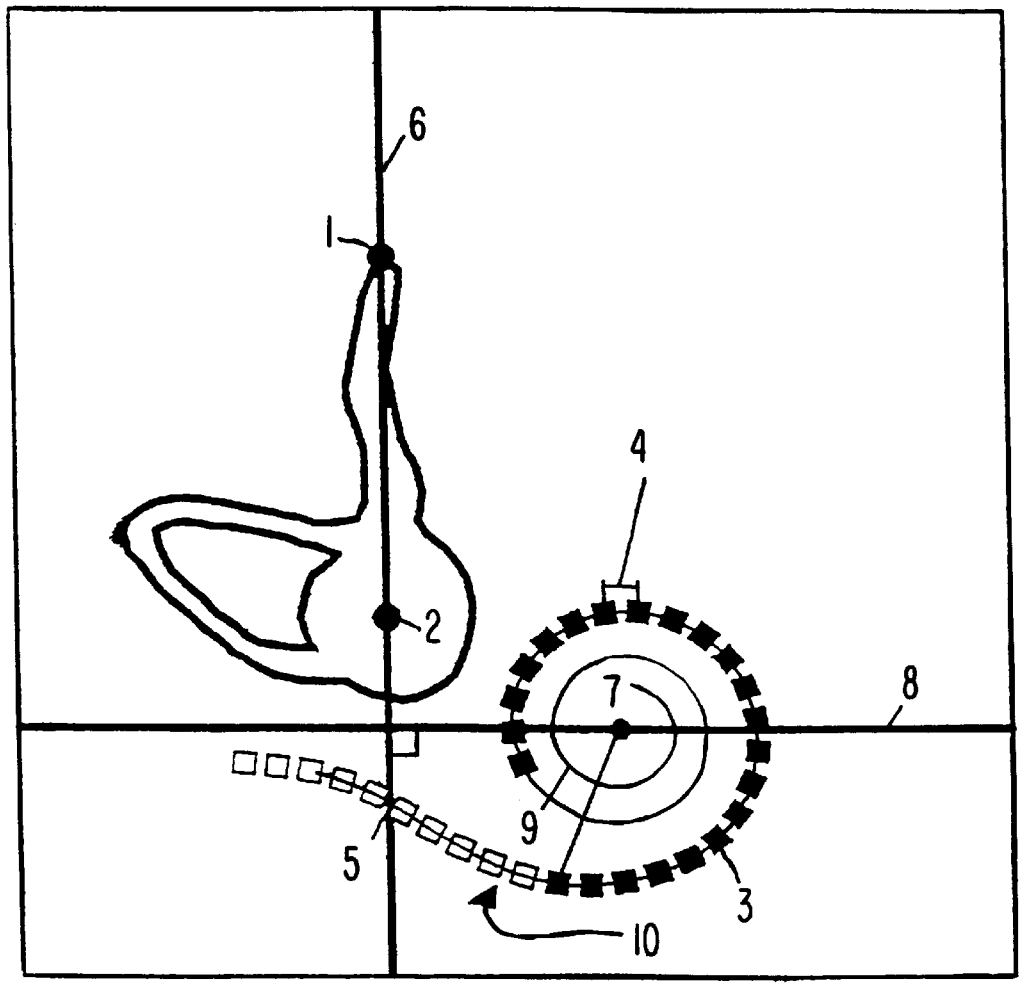
FIG. 2 is a schematic diagram of a cochlear X-ray, showing an implanted electrode array and relevant anatomical features.

Such an X-ray image is illustrated schematically in FIG. 2. Various anatomical features can be seen, including the vestibule 2, and the tip of the superior semicircular canal 1. From this X-ray the position of the round window 5 is estimated by drawing a primary reference line 6 from the tip of the superior semicircular canal 1 through the centre of the vestibule 2. If the array was originally located by insertion through the round window 5 then the round window will lie at the intersection of line 6 and the electrode array 10. A further reference line 8 is drawn from the centre of the template spiral 7 perpendicular to the primary reference line 6, relative to which angle θ 9 is measured, which will be described in more detail below. From the figure can also be seen individual electrodes 3, and interelectrode spacing 4 which will be assumed to be regular.

The method used by the processor to obtain the characteristic frequency for each electrode band of the cochlear implant in the present embodiment is as follows:

1. Calculate the size of a template cochlear spiral. The size of the template spiral is matched to that of the electrode spiral seen on the X-ray, using the counted number of electrode bands between key points on X-ray.
2. Calculate the angle θ for each electrode. The angle at the point where the array crosses the primary reference line 6 is given a mean value derived from study of X-rays of patients and implanted temporal bones, and the length around the array from the crossing point to any electrode is known. Given the size of the template spiral, the angle for any electrode can be calculated from the mathematical shape of the template spiral. The mean angle for crossing of the primary reference line by the electrode array depends on the site of insertion of the electrode array. For round window insertion, it has been found to be 13.47°. For cochleostomy insertion (through the outer wall of scala tympani) the corresponding value was 23° for insertions done in the Cochlear Implant Clinic at The University of Melbourne. It should be realised, however, that this value will vary somewhat with surgical technique.
3. Calculate, for each electrode, the percentage length along the organ of Corti corresponding to the calculated angle. This calculation uses the data of Bredberg (previously referenced).
4. Calculate the characteristic frequency for each electrode, using the percentage length along the organ of Corti and the expression of Greenwood (previously referenced).

Figure 3:
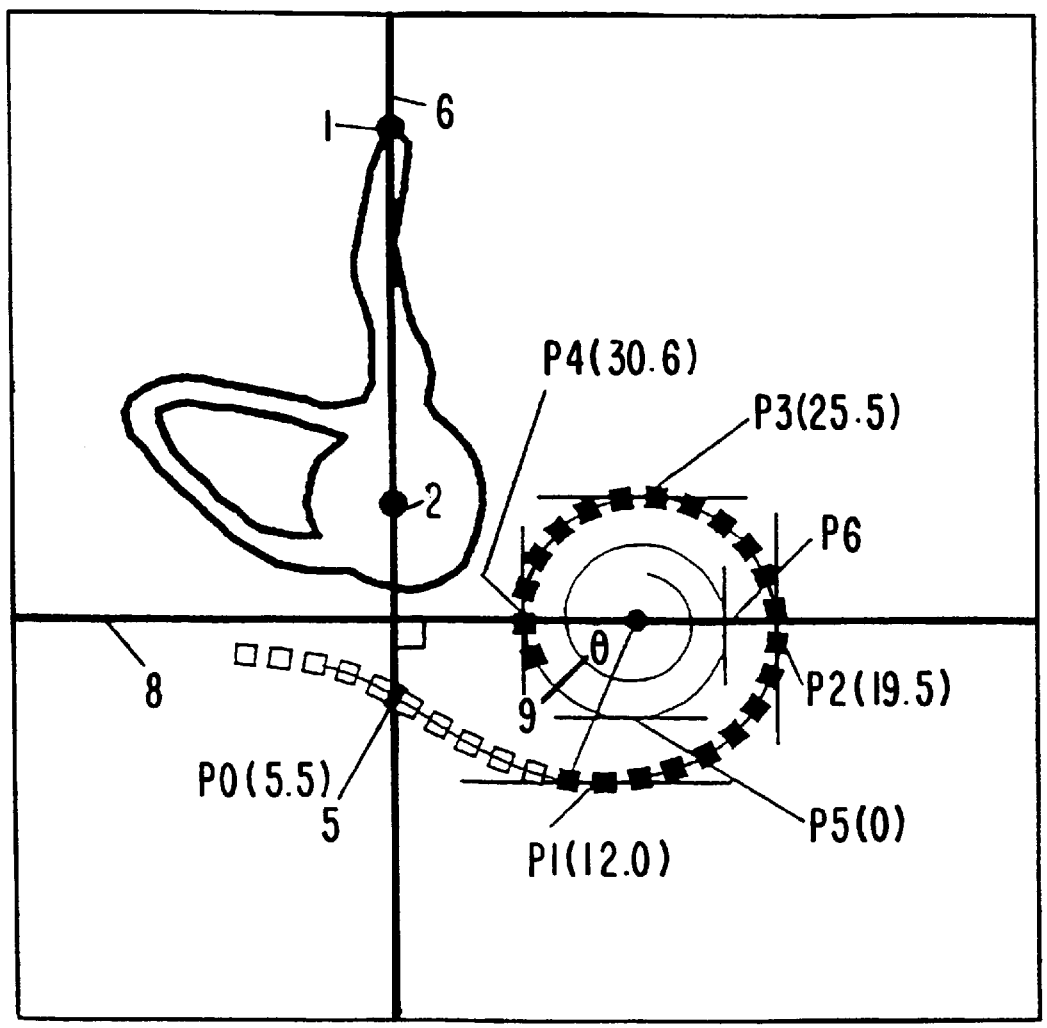
FIG. 3 is a schematic diagram of a cochlear X-ray, showing the positions of points on the electrode spiral used in the band counting procedure.

The methods and equations used to perform the calculations are as follows. The counting of electrodes commences from the physical start of the electrode array, outside the cochlea. If the array is fully inserted, then an alternative calculation using two tangent lines, to be described below, may be used. The electrodes are counted and the number reached as the electrodes cross the primary reference line is entered (point P0 in FIG. 3, count of 5.5). The counting is continued until the electrodes have passed a number of other points on the X-ray. The subsequent points at which the electrodes are counted are tangents to the array, such that they are either parallel to or at right angles to the primary reference line. They are marked as P1–P6 on FIG. 3. The process of visualising these points is facilitated by the use of a sheet of transparent plastic on which a bold line and a grid are printed. In use the operator superimposes the plastic sheet on the X-ray and aligns the bold line with the tip of the semicircular canal and the centre of the vestibule. The bold line would then be aligned with the notional primary reference line, and the tangent points could be visualised using the grid. The counting continues from point P0 to point P1 (count of 12.0 in FIG. 3), to point P2 (count of 19.5), to point P3 (count of 25.5), to point P4 (count of 30.6), etc. In FIG. 3, point P4 is the most apical point reached, and the value entered for P5 would be a default value (say, zero) to signify that the array did not reach that point. Similarly, in the general case, the value entered for the first point the array does not reach would be zero. From FIG. 3, values are P1 First tangent point (electrode count 12.0 in this example)

P2 Second tangent point (electrode count 19.5 in this example)

P3 Third tangent point (electrode count 25.5 in this example)

P4 Fourth tangent point (electrode count 30.6 in this example)

P5 Fifth tangent point (electrode count 0 in this example, indicating that this is the first point the array does not reach)

P6 Sixth tangent point (no electrode count in this example).

It will be appreciated that according to the present invention in this example only the P0 and P4 values are required. Entering further data is not essential but may provide a more accurate calculation and consistency check.

The length around the template spiral between the points where the electrode array crosses the primary reference line (P0 on FIG. 3) and the innermost tangent point (P4 in the example of FIG. 3) is calculated using a scaling factor of 1.0 in Eqns. 1 and 2 (defined below). The template spiral is given by Eqns 1 and 2, and the length around the spiral is calculated numerically using those equations and Eqn. 3 (defined below), which relates length along a curve to its polar coordinates (radius and angle). Note that the angles at the entry point and at all the tangent points are known from the shape of the template spiral. The length around the template spiral is compared with the actual length between the points 5 (PO) and P4 (in this example), as measured between electrode counts at those points. It should be noted that the distance between the centres of the electrode bands is accurately controlled during manufacture of the Cochlear Limited devices (0.75 mm), and therefore the number of bands between two points gives an accurate measure of distance. The scaling factor is then adjusted so that the theoretical length equals the measured length thus fitting the template spiral to the electrode spiral seen on the X-ray.

The angle of each electrode can then be calculated from the template spiral, as the angle at point PO (5) is known and the length around the spiral from that point to the electrode is also known. This calculation is performed numerically using Eqns 1, 2 and 3.

On completion of the data entry, a reproduction of the electrode spiral may be displayed on monitor 238 based on the angle calculations performed by the program. The graphical representation of the electrode spiral is to allow the user to verify that the information entered is correct. The displayed spiral is similar to that of FIG. 3. On FIG. 3 is marked the line 8, drawn from the centre of the template spiral perpendicular to the primary reference line, relative to which angle n (item 9) is measured.

Figure 4:
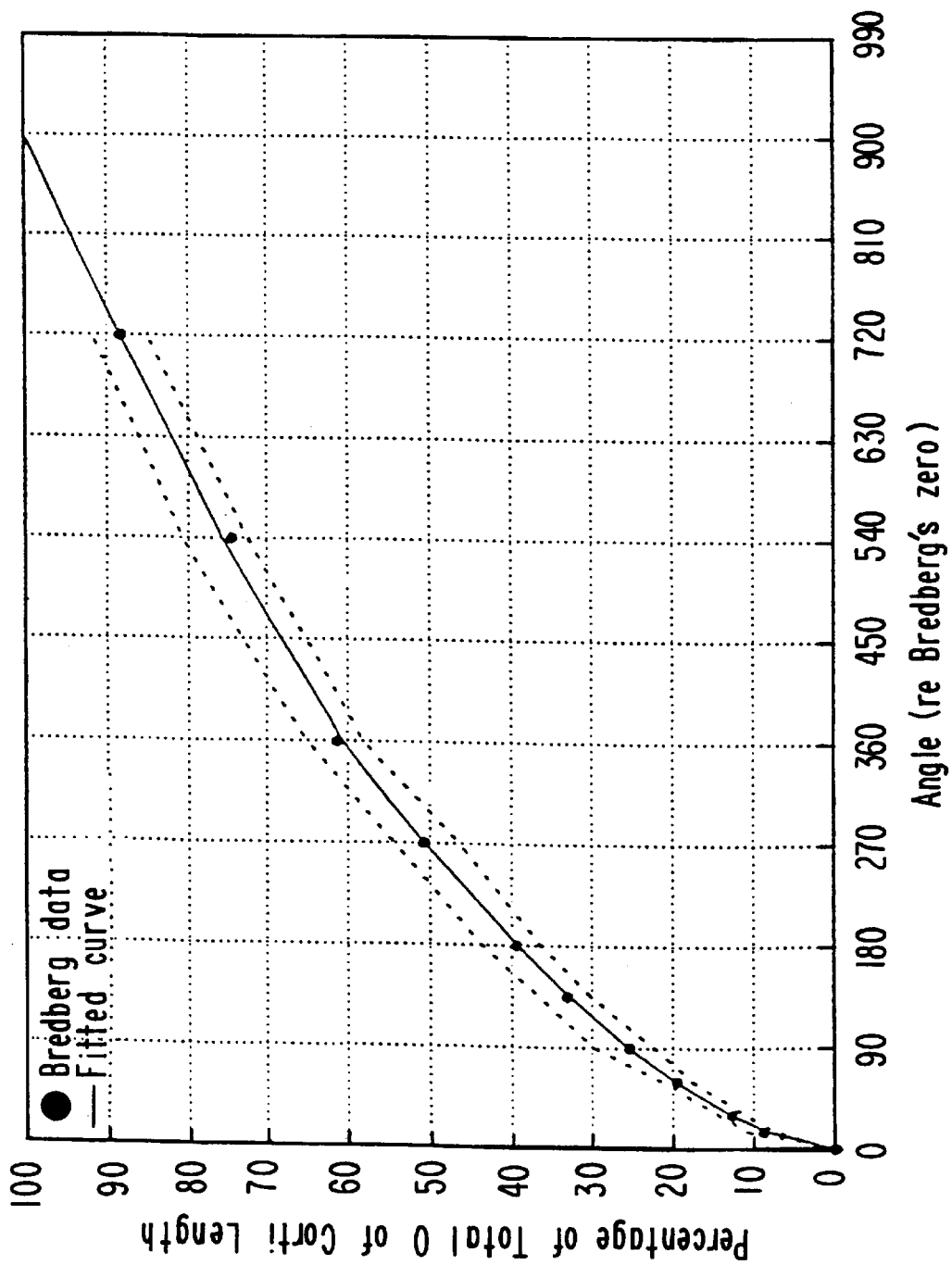
FIG. 4 is a graph showing the relationship between percentage length along the organ of Corti and the cochlear angle relative to the basal end of organ of Corti.

FIG. 4 illustrates percentage length along the organ of Corti plotted against angle (measured relative to Bredberg's zero). Filled circles indicate Bredberg's data and the solid curve was fitted to those data. Dashed curves are experimental variations in Bredberg's data. Once all the electrode angles have been determined, the data of FIG. 4 is used to convert each angle into a percentage of the length of the organ of Corti. This is done using Eqns. 4 and 5 (defined below), which closely approximate the results shown graphically by Bredberg and Eqn. 6 which relates the angles measured according to the present invention and the angles used by Bredberg (see below). The percentage of the length of the organ of Corti now enables the frequency associated with that angle (and electrode) to be calculated, using the Greenwood formula (Eqn. 7). The Greenwood formula describes the relationship between frequency and the site of maximal displacement of the basilar membrane, expressed as a percentage of the total length of the organ of Corti, measured from the apex.

Once the data entered has been accepted, further calculations are performed. The frequencies obtained for the electrodes are then plotted on a frequency versus electrode graph. The frequency allocation of the speech processor can then be adjusted to allow for the closest frequency band allocation to the calculated electrode frequency set.

The following equations, Eqn (1) and Eqn (2) describe the radial distance from the centre (approximately the modiolus) of the template spiral as a function of angle about the centre, relative to a line drawn from the centre perpendicularly to the reference line. The perpendicular line is shown as 8 on FIG. 3, and the angle n (in degree) is shown as item 9. For the angle less than 100° the spiral radius in millimetres is given by:

$$\text{Radius} = \text{Scaling Factor} * [7.9664 - 1.0252 \ln(n-5)] \quad (1)$$

For the angle in excess of 100° the radius is given by:

$$\text{Radius} = \text{Scaling Factor} * 3.762 \exp(-0.001317 n) \quad (2)$$

For a scaling factor of 1.0, the spiral of Eqn. 2 corresponds to the mean of 30 X-ray spirals of which 28 were for cochleostomy insertions (through the outer wall of scala tympani). The parameters of Eqn. 2 were established by fitting the mathematical spiral to the X-ray spirals for angle greater than 100°. Note, however, that Eqn. 1 is applicable to a round window insertion. For a cochleostomy insertion slightly different parameters would apply. As the mean values would depend slightly on surgical techniques used, it is not appropriate to specify values here. However, with respect to the present invention Eqn. 1 (as given above) is a good approximation for all cases, provided a small correction is made to the band count at the primary reference line 6, illustratively half a band.

The length along the spiral of a point on it is calculated using the expression:

$$d(\text{length})/d(\text{angle}) = \text{sqrt}\{(\text{radius})^2 + [d(\text{radius})/d(\text{angle})]^2\} \quad (3)$$

This general expression relates length along the spiral of the point to its polar coordinates, radius and angle (in radians).

Using Eqns. 1–3, angles were calculated for the reference points for the band counting procedure. The results are:

| 1) | P0 | Round window entry | 13.47° |
|---|---|---|---|
| 2) | P1 | Basal turn bottom tangent | 77.19° |
| 3) | P2 | Basal turn right tangent | 175.68° |
| 4) | P3 | Basal turn top tangent | 265.68° |
| 5) | P4 | Middle turn bottom tangent | 355.68° |
| 6) | P5 | Middle turn right tangent | 445.68° |
| 7) | P6 | Middle turn top tangent | 535.68° |
| 8) | P7 | Middle turn left tangent | 625.68° |
| 9) | P8 | Apical turn bottom tangent | 715.68° |
| 10) | P9 | Apical turn right tangent | 805.68° |
| 11) | P10 | Apical turn top tangent | 895.68° |

The Bredberg data, relating the percentage length along the organ of Corti to the angle in degrees about the modiolus can be closely approximated by the following expression. For $n_B$ from 0 to 360 degrees:

$$\text{Percentage of Total Length} = 1.4971 * n_D^{80.6292} \quad (4)$$

For $n_B$ above 360 degrees:

$$\text{Percentage of Total Length} = 2.4778 * n_B^{0.5436} \quad (5)$$

Both the percentage of total length and the angle ($n_B$) are measured relative to the basal end of the organ of Corti. Therefore, $n_B$ is not identical to n of Eqns 1, 2 and 3. n arises from the geometrical construction of the reference line, and is measured relative to a line at right angles to the reference line, while $n_B$ is measured relative to the position of the basal end of the organ of Corti. It is necessary to establish an approximate relationship between these two angles. It is shown below that angles measured in the two ways are related approximately as follows:

$$n_B = n - 10 \quad (6)$$

The Greenwood equation can be rewritten so that length along the organ of Corti is measured from the basal end, thus:

$$\text{Frequency} = 165 * \{10^{[0.0210 * (100 - percentage)]} - 0.8788\} \quad (7)$$

Figure 6:
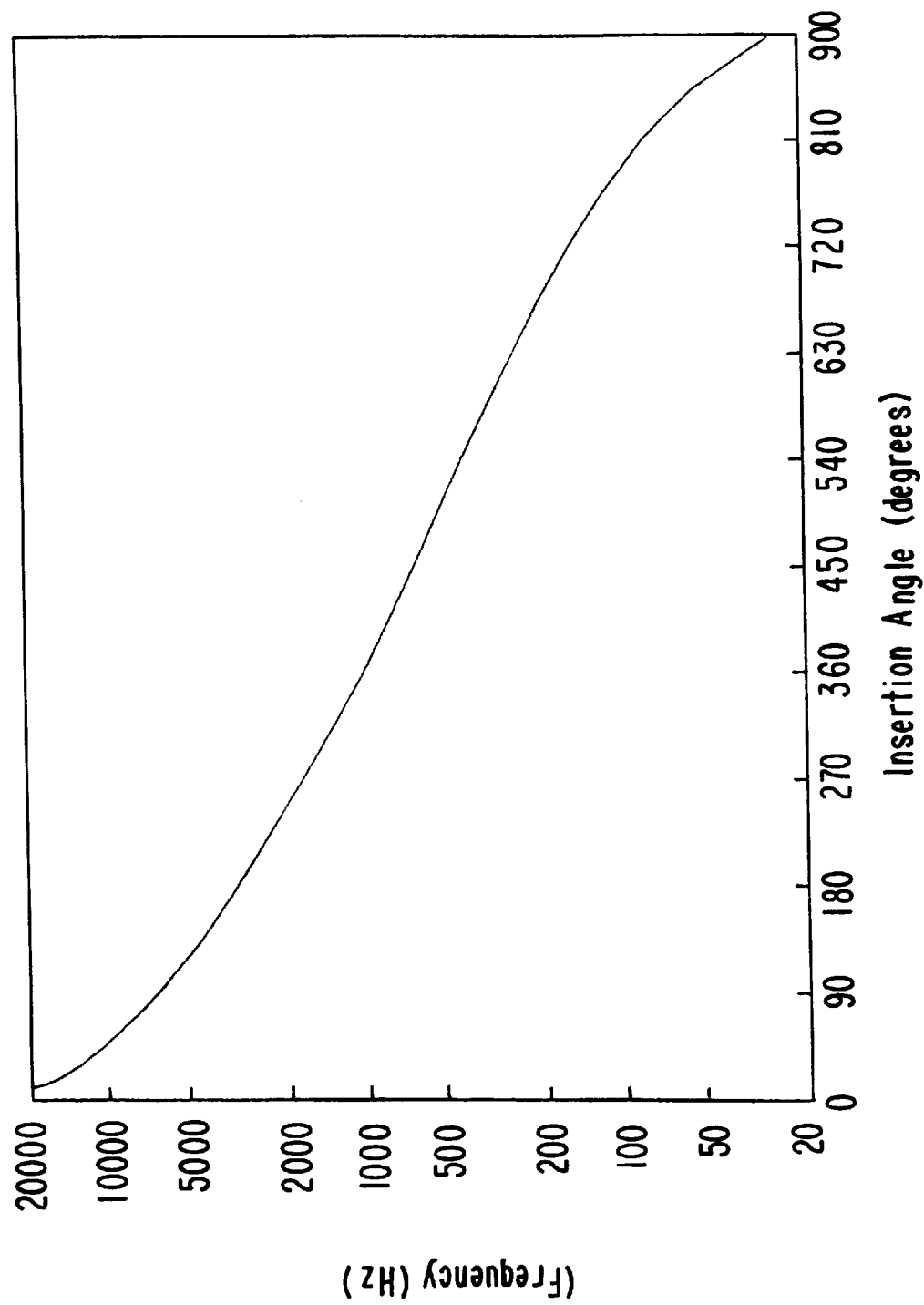
FIG. 6 is a graph plotting frequency against insertion angle.

The relationship between frequency of maximum displacement and angle is plotted in FIG. 6.

Figure 5:
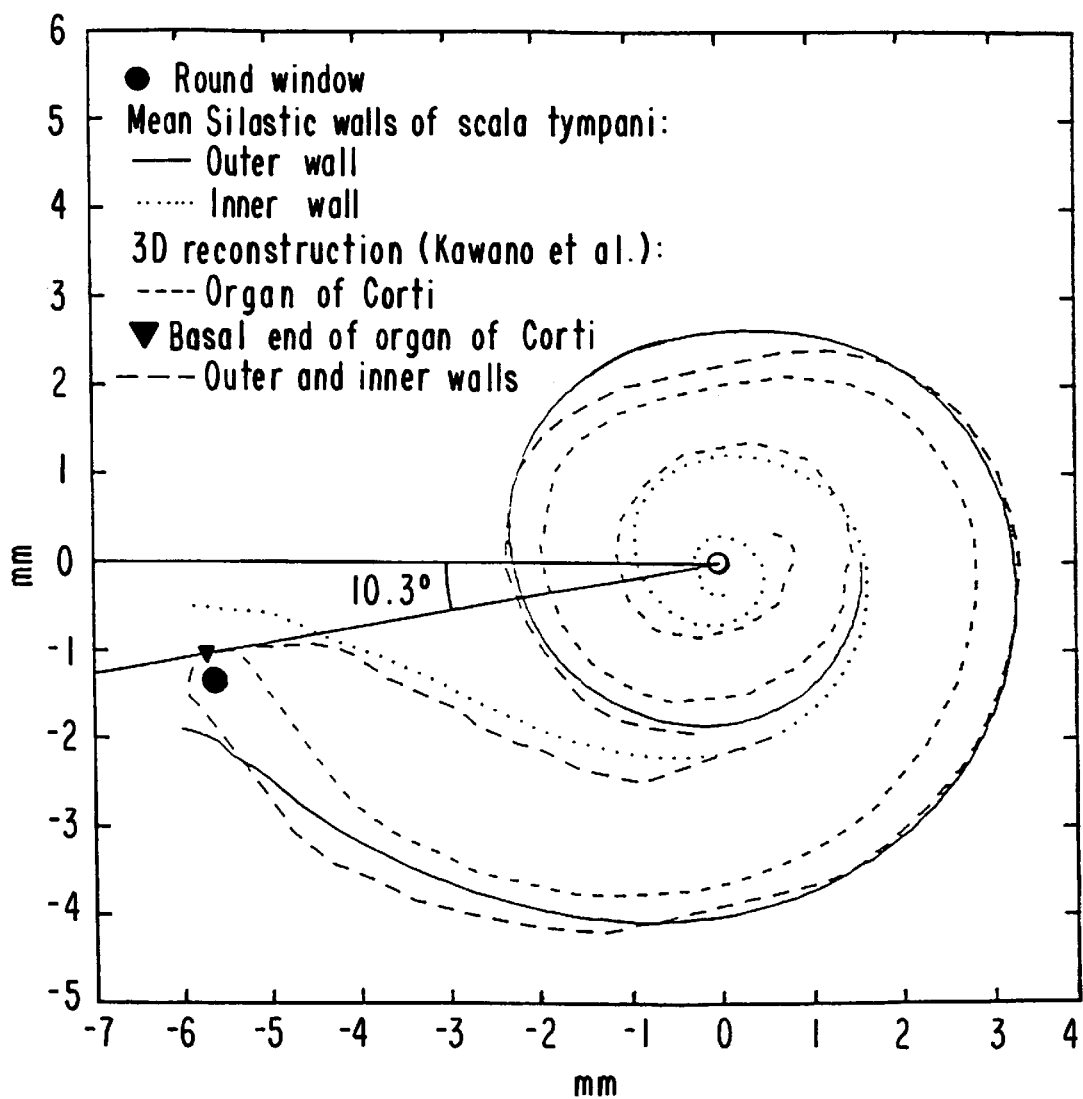
FIG. 5 is a diagram showing the relationship between angle as measured in the present method and in the method of Bredberg.

In order to make use of the Bredberg data relating percentage length along the organ of Corti to angle, it is necessary to relate approximately the angular measurements of Bredberg's method and the angles used in the present method. For this purpose, two sets of data were compared graphically as shown in FIG. 5. One set of data was derived from 11 Silastic® moulds of scala tympani and comprised mean outer and inner walls of the scala and the mean round window position. These data were presented in the angular framework of the present method. The second set of data was taken from a 3D reconstruction of a cochlea (from Kawano, A., Seldon H. L., and Clark, G. M. "Computer-aided three-dimensional reconstruction in human cochlear maps: measurement of the lengths of organ of Corti, outer wall, inner wall, and Rosenthal's canal," Ann. Otol. Rhinol. Laryngol. (in press)). The 3D data comprised outer and inner walls of scala tympani and the organ of Corti, including the position of the basal end. The position of the round window could be inferred in the 3D data. The size, position and rotation of the 3D data were adjusted to be consistent with the data from the Silastic® moulds. As the position of the basal end of the organ of Corti corresponds to zero degrees in Bredberg's method, this figure provides an estimate of the relationship between the angular zeros in the measurement schemes. The approximate relationship is given in Eqn. 6.

In order to be able to calculate angles for the electrode bands, it is necessary to determine a centre point about which to measure the angles. In the development of the inventive method, the positions of electrode bands on the X-rays were originally digitised, and various spiral shapes were fitted to the electrode positions, thus yielding estimates for the spiral centre. The shape of Eqns. 1 and 2 was found to provide a good fit to the electrode positions.

Therefore, given that template shape, the centre may be estimated for a particular electrode X-ray by doing a least squares fit of the template to the digitised positions of the bands. The variables in this fitting process are (i) the size of the template and (ii) the x and y positions of the template. Doing this fit gave a good estimate of the centre and allowed automatic calculation of individual angles of electrodes. The final method as described above has the considerable advantage of requiring much less data input, in principle only two numbers, namely the electrode band counts at the principal reference line and at the most apical tangent point. Because the angle at the principal reference line crossing is known, and the angles at the tangent points are known, these two band counts fully determine the fitting of the template to the data. The data determine the size of the template spiral, while the position of the spiral centre does not need to appear explicitly in the calculations.

The method may be applied to other electrode arrays, for example an array that might follow the inner wall of the scala tympani, rather than the outer wall as in this case. For the method to be used with a different electrode array, ideally one would deduce a template spiral that reliably represented the spiral presented on the X-ray by the image of the electrode array. The template could be a numerical relationship between radius and angle, that is, there is no need to provide an analytical expression for the relationship. However, the exponential spiral shape used here (Eqn. 2) is very suitable for the description of the shape of the inner wall of the scala tympani, for all but the most basal region of the cochlea, and would therefore be suitable for an array that followed the inner wall. Eqn. 1 could probably be used for the basal region. However, appropriate parameters of both Eqn. 1 and Eqn. 2 would need to be established. The parameters may be readily determined using the techniques described above.

The inventive technique requires a knowledge of the separations between the electrodes along the array. For the Cochlear Limited array, the electrode separation is accurately maintained at 0.75 mm.

Figure 7A:
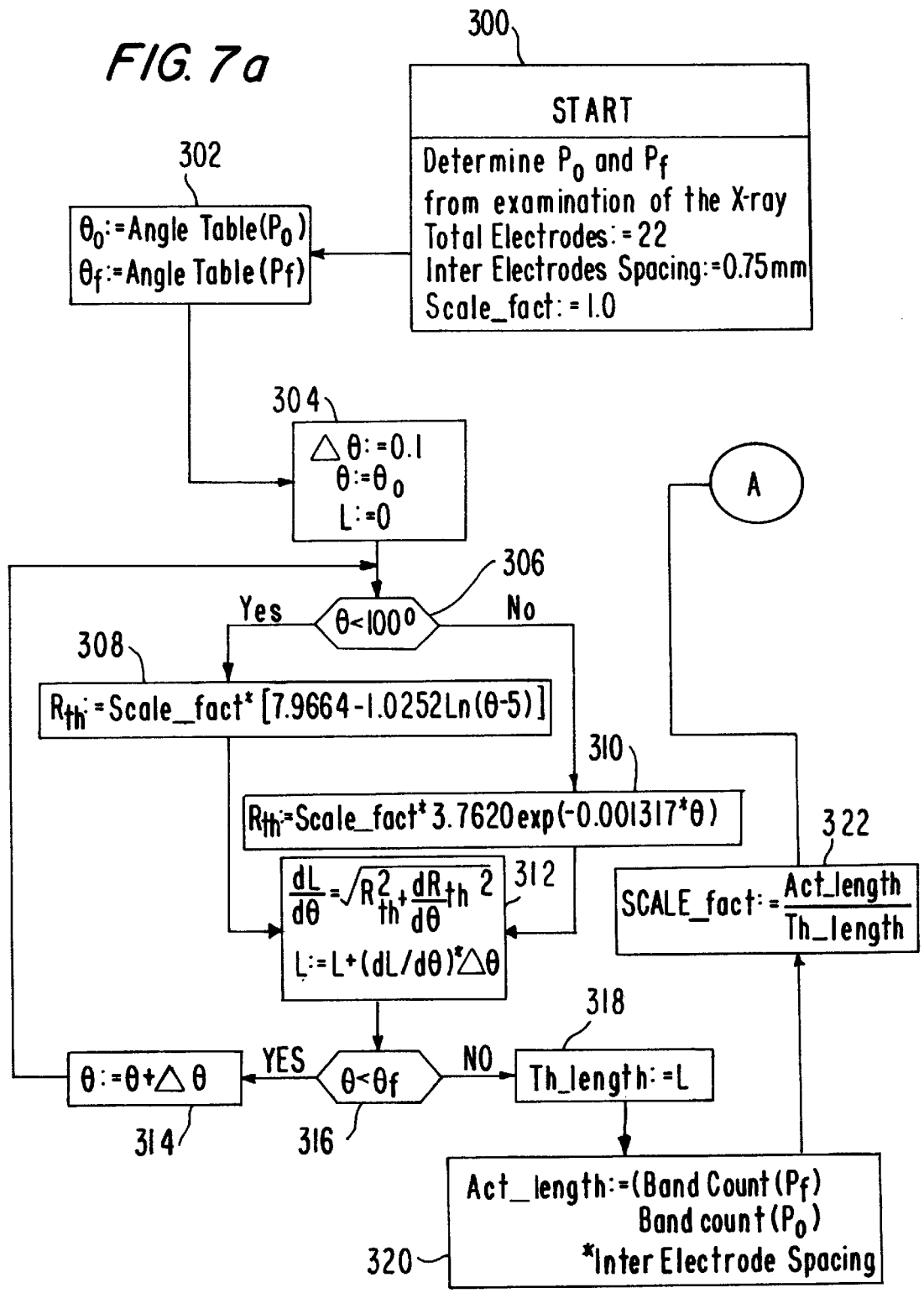
FIG. 7a is a first section of a flowchart illustrating one software implementation of the present invention.
Figure 7B:
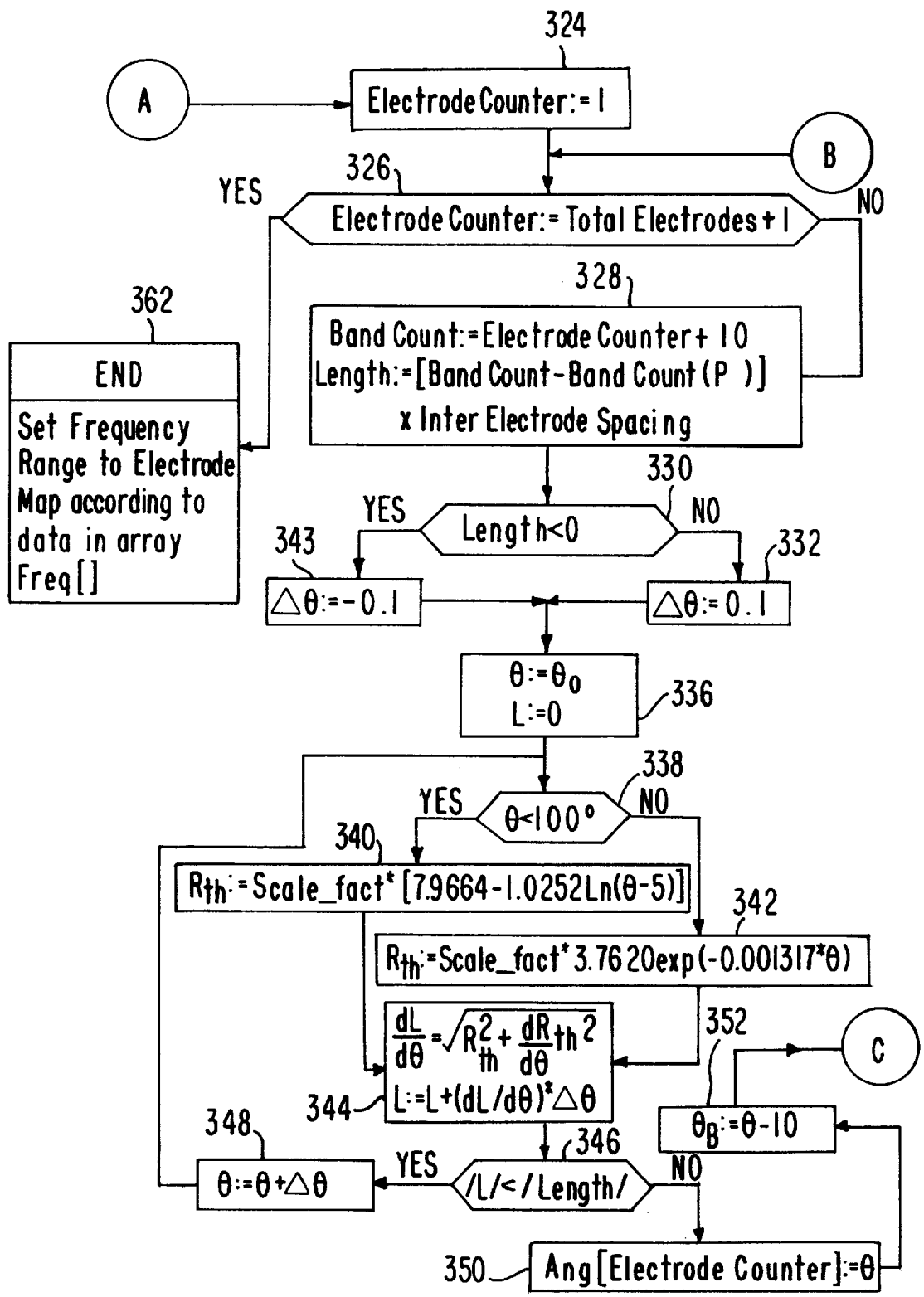
FIG. 7b is a second section of a flowchart illustrating one software implementation of the present invention.
Figure 7C:
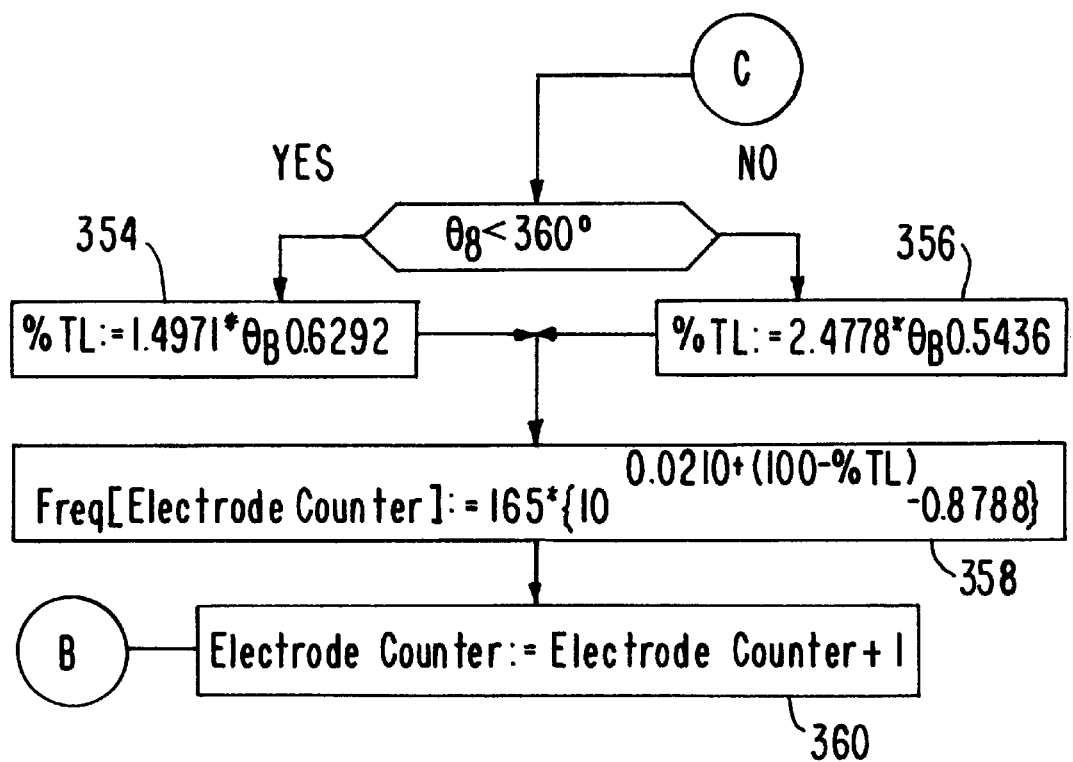
FIG. 7c is a third section of a flowchart illustrating one software implementation of the present invention.

FIGS. 7a, 7b, 7c illustrate one software implementation of the method described above. Such a program would be run by the processing means 234 of FIG. 1. Input data are $P_o$ and $P_t$, determined from the X-ray as shown in FIG. 2, and other information which characterises the array. The last step of the process is shown in the box 362, marked END, and is to set the frequency range to electrode map 238 on the basis of the calculated characteristic frequency values in the array Freq[]. The flowchart depicted in FIGS. 7a–7c is to be read on the understanding that the commands flow from figure to figure at the points marked with identical capital letters.

Referring to FIG. 7a the flowchart begins with start box 300 by which the first step is to locate the landmark points at which the electrode array crosses the primary reference line $P_o$ (item 5 of FIG. 3) and the final tangential point of the array $P_t$ (point P4 of FIG. 3). Other data concerning the total number of electrodes in the array and the spacing between them is also entered. The scale factor variable Scale_fact is initialised to 1.0. In box 302 the angles $n_o$ and $n_f$ which correspond to the angular positions of $P_o$ and $P_f$ are determined from a pre-calculated table of angles such as the one described earlier in reference to equations 1 to 3. The remainder of the flowchart of FIG. 7a is concerned with finding the length around a template spiral between the angles $n_o$ and $n_f$ and comparing this length with the actual length around the electrode array spiral between $P_o$ and $P_f$ in order to determine a scaling factor. In box 304 the variable n is initialised to $n_o$ and the variable L, representing the length around the template spiral from $n_o$ to $n_f$, to zero. $\Delta n$ represents a small incremental change in n and is initialised to 0.1.

The polar coordinates $(R_{th}, n)$ along the template spiral are calculated according to the equations in boxes 308 and 310 being previously described equations (1) and (2). At box 312 the distance along the template spiral from $n_o$ to $\Delta n$ is calculated by numerically solving the differential equation for the distance along a curve given in polar coordinates. Methods for solving such equations are standard in the art of mathematical computing and will not be discussed in detail here. The distance along the spiral template is accumulated in the variable L and the variable n is incremented (box 314) until it is slightly greater than $n_f$ (box 316). The length of the template spiral is then stored in variable Th_length (box 318). At box 320 the number of electrode bands from $P_f$ to $P_o$ is calculated and converted to a distance by multiplying it by the InterElectrodeSpacing variable. The actual distance between the two landmark points $P_f$ and $P_o$ on the electrode array is stored in the variable Act_length. At box 322 the ratio of the actual length of the cochlear electrode array spiral, between $P_f$ and $P_o$, to the length previously calculated along the template spiral by the angle subtended by $P_f$ and $P_o$ is calculated and stored in variable Scale_fact.

Referring now to FIG. 7b the section of the flowchart therein depicted scales the template spiral to match the electrode array spiral and calculates the angular position of an electrode on the template spiral according to its position on the electrode array relative to $P_o$.

At box 324 the ElectrodeCounter variable is initialised to 1 in order to commence calculation of the angular position of the first electrode. At box 328 the bandnumber of the electrode is calculated from its electrode number. For example it can be seen with reference to FIG. 3 that electrode 1(item 13) corresponds to band 11 as there are ten non-electrode stiffening bands located basal to the first stimulating electrode. The length along the array of the first spiral to the electrode with number ElectrodeCounter is determined in box 328 by finding the number of bands between the first landmark point $P_o$ and the electrode under consideration. As an example, for the first electrode of FIG. 3 the ElectrodeCounter variable is set to 1. The BandCount variable is set to 11 being the sum of the ElectrodeCounter value and the number of stiffening bands. The length variable is the distance of the first electrode along the cochlear electrode array and equals the product of the interelectrode spacing with, the difference of the BandCount variable (11) and the band number at which the electrode array crossed the primary reference line which was 5.5 for the example depicted in FIG. 3.

Given the distance of the electrode along the electrode spiral and the equation of the scaled template spiral the corresponding angular position on the template spiral can then be calculated for electrode number 1. This value is calculated in similar fashion to that described with reference to the loop of FIG. 7a. The value for n which corresponds to the postion of the electrode on the template spiral is stored in data array Ang[] at box 350. At box 352 the angle n is related to the Bredberg angle $n_B$ as previously described.

Referring now to FIG. 7c, therein is depicted a section of the flowchart in which the percentage length along the organ of Corti for each electrode is calculated from its angle n in degrees about the modiolus of the electrode as previously determined (boxes 354, 356). The percentage length is then used to calculate the theoretical characteristic frequency of the electrode at box 358 and the result is stored in an indexed data array Freq[]. The program then increments the ElectrodeCounter variable at box 360 and the electrode position frequencies are calculated and stored for each electrode until the condition of decision box 326 of FIG. 7b is satisfied thereby signifying that the characteristic frequencies of all the electrodes have been determined.

The final step of the procedure is depicted at box 362 by which the electrode array characteristic frequencies stored in Freq[] are used to set the Frequency Band to Electrode Map 223 of the cochlear prosthesis.

It will be appreciated that alternative means software implementations could be used if desired. Variations and additions may be made to the method and product disclosed within the general inventive concept.

We claim:

1. An apparatus for configuring a frequency range to electrode map disposed in a data storage of a cochlear implant prosthesis, the frequency range to electrode map containing frequency range to electrode mapping data, comprising:

a) processing means for processing electrode location data, the electrode location data describing the location of at least two electrodes relative to a cochlea, the electrodes being components of an electrode array, the processing means generating characteristic frequency data and being adapted to determine from said characteristic frequency data said frequency range to electrode map to relate a characteristic frequency to each electrode;

b) input means for conveying the electrode location data to the processing means;

c) interface means for transferring the frequency range to electrode map to the data storage;

wherein the processing means generates the characteristic frequency data according to a characteristic frequency model, wherein the characteristic frequency data includes characteristic frequencies of electrodes of the electrode array, the characteristic frequency of an electrode corresponding to the estimated frequency of maximal displacement of the basilar membrane of the cochlea, according to the characteristic frequency model, at the location of said electrode of the electrode array.

2. The apparatus of claim 1 wherein, the processing means is integrated with the cochlear implant prosthesis and wherein said interface means comprises a bus connecting the processing means to the data storage.

3. The apparatus of claim 1, wherein said input means includes means for deriving electrode location data from a medical diagnostic image of an implanted electrode array.

4. The apparatus of claim 3, further comprising a scanner for deriving said electrode location data from a hardcopy image.

5. The apparatus of claim 3, further comprising image processing means for deriving the electrode location data from said medical diagnostic image.

6. A method for setting a frequency range to electrode map of a cochlear implant prosthesis including the steps of:

a) determining two fitting values by reference to an implanted electrode array the electrode array being implanted within a cochlea;

b) matching a template cochlear spiral to said electrode array according to the fitting values;

c) determining the position of each electrode of said electrode array relative to the cochlea from the template cochlear spiral and known dimensions of the type of implanted array;

d) calculating a characteristic frequency for each electrode from the position of each electrode relative to the cochlea according to a mathematical model of the characteristic frequency characteristics of a cochlea for each of the electrodes;

e) setting the frequency range to electrode map of the cochlear implant prosthesis on the basis of the characteristic frequencies calculated in the previous step.

7. A method according to claim 6, wherein the fitting values are determined with reference to a diagnostic medical image in which the implanted electrode array and anatomical structures of the inner ear are visible.

8. A method according to claim 7, wherein one of said two fitting values is determined by the number of electrodes extending outside the round window, the other of said two fitting values being the number of electrodes extending from the round window to the most apical of a set of geometrically defined points on the diagnostic medical image.

9. The method according to claim 8, wherein said set of geometrically defined points comprises those points on the electrode array intersecting a tangent to the electrode array wherein said tangent is either parallel to or normal to a primary reference line, said primary reference line being determined by anatomical landmarks of the inner ear.

10. The method according to claim 8, wherein step (c) further comprises estimating the center of the cochlear spiral; defining a reference line through said estimated center; calculating the angle defined by each electrode relative to said reference line; and calculating, for each electrode, the percentage length along the organ of Corti corresponding to the calculated angle.

11. A product for determining characteristic frequency for electrodes in an implanted intracochlear electrode array based on an diagnostic medical image, said product being provided with inputs including for a given implanted array a first value being the number of electrodes extending outside the round window, and a second value being the number of electrodes extending from the round window to the most apical of a set of geometrically defined points on the diagnostic medical image to which the image of the array extends, means for identifying the most apical of said points, said product including means for determining the position of the implanted electrodes by reference to a predefined reference shape and predefined dimensions of the electrode array, means for mapping said electrode positions to corresponding characteristic frequencies, and means for outputting a set comprising characteristic frequencies for each electrode.

12. A product according to claim 11, wherein said means for determining the position of the implanted electrodes calculates the size of a template cochlear spiral with reference to a mathematical description of the shape of the cochlear spiral.

13. A product according to claim 12, wherein said means for determining the position of the implanted electrodes further determines the angle defined by each electrode relative to the estimated centre of the cochlear spiral and a predefined reference line passing through said spiral, and calculates, for each electrode, the percentage length along the organ of Corti corresponding to the calculated angle.

14. A product according to claim 13, wherein said means for mapping said electrode positions to corresponding characteristic frequencies calculates the characteristic frequency for each electrode using the percentage length along the organ of Corti and a predefined relationship with characteristic frequency.

15. An apparatus for configuring a cochlear implant having an electrode array formed of at least two electrodes and a data storage containing a frequency range to electrode map relating a characteristic frequency to each of said electrodes, said apparatus comprising:

an input arranged to receive location data indicative of the location of said electrodes within the cochlea of a patient;

a data processor coupled to said input to receive said location data, said data processor being arranged and constructed to generate said map from said location data in accordance with a characteristic frequency model which relates the characteristic frequency of any electrode to an estimated frequency of a maximal displacement of the basilar membrane at the location of that electrode; and an interface coupled between said data processor and said data storage to transfer said map to said data storage.

16. The apparatus of claim 15 wherein said data processor is integral with said cochlear implant and said interface includes a bus connecting said data processor to said data storage.

17. The apparatus of claim 15 wherein said input includes an image translator adapted to derive said location data from a medical diagnostic image of said electrode array.

18. The apparatus of claim 17 wherein said image translator is constructed and arranged to derive said location data from a hard copy of said medical diagnostic image.

* * * * *